US 008020308B2

(12) United States Patent  (10) Patent No.: US 8,020,308 B2
Lee et al.  (45) Date of Patent: Sep. 20, 2011

(54) NON-DESTRUCTIVE INSPECTION SYSTEM HAVING SELF-ALIGNING PROBE ASSEMBLY

(75) Inventors: Byungwoo Lee, Rexford, NY (US); Yanyan Wu, Houston, TX (US); Nicholas Joseph Kray, Blue Ash, OH (US)

(73) Assignee: General Electric Company, Niskayuna, NY (US)

( * ) Notice: Subject to any disclaimer, the term of this patent is extended or adjusted under 35 U.S.C. 154(b) by 217 days.

(21) Appl. No.: 12/475,101

(22) Filed: May 29, 2009

(65) Prior Publication Data

US 2010/0305876 A1  Dec. 2, 2010

(51) Int. Cl.
  *G01R 1/067* (2006.01)
  *G01D 5/28* (2006.01)
  *G01B 5/012* (2006.01)
  *G01B 7/012* (2006.01)
(52) U.S. Cl. ................. 33/503; 33/556; 33/572
(58) Field of Classification Search .................. 33/503, 33/556, 557, 558, 572, 501.04
  See application file for complete search history.

(56) References Cited

U.S. PATENT DOCUMENTS

| | | | |
|---|---|---|---|
| 4,949,073 A | 8/1990 | Voosen | |
| 5,040,306 A * | 8/1991 | McMurtry et al. | 33/556 |
| 5,109,610 A * | 5/1992 | Johnson | 33/559 |
| 5,207,005 A * | 5/1993 | Amos et al. | 33/501.04 |
| 5,321,895 A * | 6/1994 | Dubois-Dunilac et al. | 33/556 |
| 5,402,582 A | 4/1995 | Raab | |
| 5,491,904 A | 2/1996 | McMurtry | |
| 5,669,152 A | 9/1997 | McMurtry | |
| 5,797,191 A | 8/1998 | Ziegert | |
| 5,939,647 A * | 8/1999 | Chinn et al. | 73/864.71 |
| 6,086,283 A | 7/2000 | Ziegert | |
| 6,272,908 B1 | 8/2001 | Boccuzzi et al. | |
| 6,341,153 B1 | 1/2002 | Rivera et al. | |
| 6,504,363 B1 | 1/2003 | Dogaru et al. | |
| 6,854,193 B2 | 2/2005 | Lotze | |
| 6,894,492 B1 * | 5/2005 | Dziech | 324/238 |
| 7,228,642 B2 | 6/2007 | Enderle et al. | |
| 7,337,685 B2 | 3/2008 | Baylis et al. | |
| 2002/0128790 A1 | 9/2002 | Woodmansee | |
| 2004/0153260 A1 | 8/2004 | Suh et al. | |
| 2004/0194331 A1 | 10/2004 | Haimer | |
| 2005/0276466 A1 | 12/2005 | Vaccaro et al. | |
| 2007/0044336 A1 | 3/2007 | Ikubo et al. | |
| 2008/0075227 A1 | 3/2008 | Christoph et al. | |

(Continued)

FOREIGN PATENT DOCUMENTS

EP  0426492 B1  6/1995

(Continued)

OTHER PUBLICATIONS

Yanyan Wu et al., "Multi-Modality Inspection Method With Data Validation and Data Fusion," U.S. Appl. No. 11/945,456, filed Nov. 27, 2007.

(Continued)

*Primary Examiner* — R. A. Smith
(74) *Attorney, Agent, or Firm* — Penny A. Clarke

(57) ABSTRACT

An inspection system comprises a sensor configured to acquire inspection data of the object, a motion control device, a joint assembly coupled to the motion control device, and a probe housing coupled to the joint assembly and configured to hold the sensor. The inspection system further comprises a compliant element coupled to the probe housing and configured to cooperate with the joint assembly and the motion control device to position the sensor relative to the object. A self-aligning probe assembly is also presented.

20 Claims, 3 Drawing Sheets

U.S. PATENT DOCUMENTS

| | | |
|---|---|---|
| 2008/0127501 A1 | 6/2008 | Eaton et al. |
| 2008/0148585 A1 | 6/2008 | Raab et al. |
| 2009/0013548 A1 | 1/2009 | Ferrari |
| 2009/0083985 A1 | 4/2009 | Ferrari |
| 2009/0112509 A1 | 4/2009 | Batzinger et al. |
| 2009/0136114 A1* | 5/2009 | Wu et al. ............ 382/141 |
| 2009/0138231 A1* | 5/2009 | Little et al. .......... 702/152 |
| 2010/0205816 A1* | 8/2010 | Wu et al. ............ 33/503 |
| 2010/0207619 A1* | 8/2010 | Wu et al. ............ 324/238 |

FOREIGN PATENT DOCUMENTS

| | | |
|---|---|---|
| EP | 1262733 B1 | 4/2002 |
| WO | 8500651 | 2/1985 |
| WO | 9507793 | 3/1995 |

OTHER PUBLICATIONS

Francis Howard Little et al., "Inspection Artifacts, Systems and Methods for Fusing Multi-Modality Inspection Data ," U.S. Appl. No. 11/946,244, filed Nov. 28, 2007.

Yanyan Wu et al., "Method and System for Integrating Eddy Current Inspection With a Coordinate Measuring Device," U.S. Appl. No. 12/372,881, filed Feb. 18, 2009.

Yanyan Wu et al., "Method and System for Multimodal Inspection With a Coordinate Measuring Device," U.S. Appl. No. 12/372,853, filed Feb. 18, 2009.

GB1008667.6 Search Report, Aug. 15, 2010.

* cited by examiner

NON-DESTRUCTIVE INSPECTION SYSTEM HAVING SELF-ALIGNING PROBE ASSEMBLY

BACKGROUND

This invention relates generally to non-destructive inspection systems. More particularly, this invention relates to non-destructive inspection systems having self-aligning probe assemblies.

Non-destructive inspection of structures involves examining a structure without harming, or requiring significant disassembly of the structure. Non-destructive inspection is advantageous for many applications in which inspection of the exterior and/or interior of a structure is required. For example, non-destructive inspection is commonly utilized in the aircraft industry to inspect aircraft structures for many types of internal or external damage to the structure. Metallic aircraft structures are typically inspected for corrosion and/or cracking, particularly near fasteners in the structure. Composite structures are typically inspected for many types of damage, such as delamination, occurring anywhere on or within the composite material.

Various types of sensors may be utilized to perform non-destructive inspection. The sensors may move on structures to be examined, and receive inspection data regarding the structures. In some applications, in order to improve the inspection accuracy, the sensors may be required to contact and to be substantially normal or perpendicular to surfaces of the structures to be inspected.

Therefore, it would be desirable to provide non-destructive inspection systems that have self-aligning probe assemblies to align the sensors relative to the surfaces of the structures to be inspected.

BRIEF DESCRIPTION

An inspection system for performing non-destructive inspection of an object is provided in accordance with one embodiment of the invention. The inspection system comprises a sensor configured to acquire inspection data of the object, a motion control device, a joint assembly coupled to the motion control device, and a probe housing coupled to the joint assembly and configure to hold the sensor. The inspection system further comprises a compliant element coupled to the probe housing and configured to cooperate with the joint assembly and the motion control device to position the sensor relative to the object.

A self-aligning probe assembly is provided in accordance with another embodiment of the invention. The self-aligning probe assembly comprises a joint assembly, a probe housing coupled to the joint assembly and configured to hold the sensor, and a compliant element coupled to the probe housing and configured to cooperate with the joint assembly to facilitate aligning the sensor to contact and to have an angle in a range of 90+/−15 degrees with an inspected surface of an object.

BRIEF DESCRIPTION OF THE DRAWINGS

The above and other aspects, features, and advantages of the present disclosure will become more apparent in light of the subsequent detailed description when taken in conjunction with the accompanying drawings in which.

DETAILED DESCRIPTION OF THE INVENTION

Embodiments of the present disclosure are described herein with reference to the accompanying drawings. In the subsequent description, well-known functions or constructions are not described in detail to avoid obscuring the disclosure in unnecessary detail.

Figure 1:
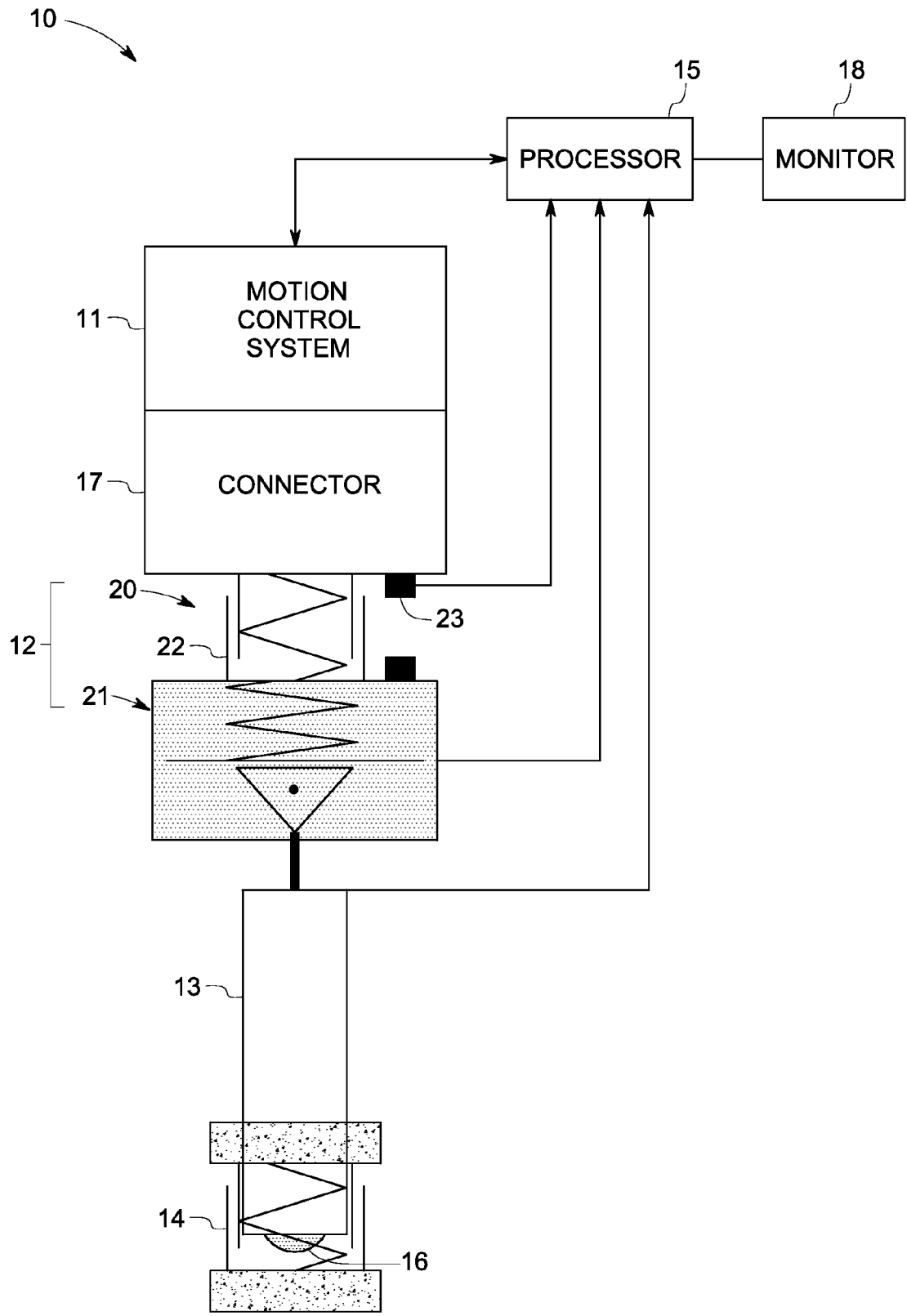
FIG. 1 is a schematic diagram of an inspection system in accordance with one embodiment of the invention.

FIG. 1 depicts a schematic diagram of an inspection system 10 in accordance with one embodiment of the invention. As illustrated in FIG. 1, the inspection system 10 comprises a motion control device 11 and a self-aligning probe assembly (not labeled). A sensor 16 is held in the self-aligning probe assembly, and the self-aligning probe assembly comprises a joint assembly 12, a probe housing 13, and a compliant element 14. Additionally, the inspection system 10 further comprises a processor 15.

For the illustrated arrangement, the motion control device 11 and the self-aligning probe assembly communicate with the processor 15. The inspection system 10 further comprises a connector 17 coupled to the motion control device 11. One end of the joint assembly 12 of the self-aligning probe assembly is connected to the motion control device 11 via the connector 17. The other end of the joint assembly 12 is connected to the probe housing 13. A free end (not labeled) of the probe housing 13 is connected to the compliant element 14. In certain examples, the connector may indicate any suitable technique to couple the joint assembly 12 to the motion control device 11. In one non-limiting example, the connector 17 may comprise an index head, sold under the tradename PH10M, by Renishaw, of Gloucestershire, United Kingdom.

As illustrated in FIG. 1, the sensor 16 is held in the probe housing 13 of the self-aligning probe assembly. In embodiments of the invention, the sensor 16 may comprise an ultrasound (UT) sensor, an eddy current (EC) sensor, an optical sensor, or any other suitable sensor to perform desired inspections. For example, the ultrasound sensor may have the capability to inspect internal geometry or defects of an object. The eddy current sensor may have the capability to identify surface or near surface defects of an object. Additionally, for some arrangements, more than one sensor may be employed in the inspection system 10, and the one or more sensors may have the same measurement capabilities, or may have more than one measurement capability to perform desired inspections.

In the illustrated example, the probe housing 13 comprises a hollow columnar shape to accommodate the sensor 16 therein. Alternatively, the probe housing 13 may have any other shape suitable for holding the sensor 16. In certain examples, the inspection system 10 may comprise more than one probe housing to hold more than one sensor having the same or different measurement capabilities.

In some embodiments, the motion control device 11 is configured to move the self-aligning probe assembly so as to move the sensor 16 to perform non-destructive inspection of an object. For the illustrated arrangement, the motion control device 11 comprises a coordinate measurement machine (CMM). In other examples, the motion control device 11 may comprise any other suitable device configured to control the movement of the self-aligning probe assembly.

The compliant element 14 is configured to transfer forces to the self-aligning probe assembly to position the sensor 16 relative to a surface of an object. In some applications, the sensor 16 may be positioned to be perpendicular to the inspected surface of the object. In other applications, the sensor 16 may be positioned to be off by a few degrees, for example about 5 or 15 degrees, from the normal of the inspected surface of the object. That is, in certain embodiments, the sensor 16 may be aligned to the inspected surface of the object with an angle in a range of 90+/−5 degrees or in a range of 90+/−15 degrees. In one non-limiting example, the sensor 16 may be aligned to the inspected surface of the object with an angle in the range of 90+/−5 degrees. Additionally, in some examples, the compliant element 14 may have one degree of freedom (1-DOF). In certain examples, the compliant element 14 may deform under pressure and restore itself in the absence of applied forces.

As depicted in FIG. 1, the compliant element 14 is assembled onto the end of the probe housing 13 with an upper end thereof. In one non-limiting example, the upper end comprises an internal thread to be detachably fixed on an external thread on a distal end of the probe housing 13. Alternatively, the compliant element 14 may be assembled onto the probe housing 13 using other techniques. In some applications, the compliant element 14 may be unitary with the probe housing 13. For the illustrated arrangement, the compliant element 14 is hollow and comprises a cylindrical linear guide with a spring (not labeled) or other elastic element therein.

Figure 2:
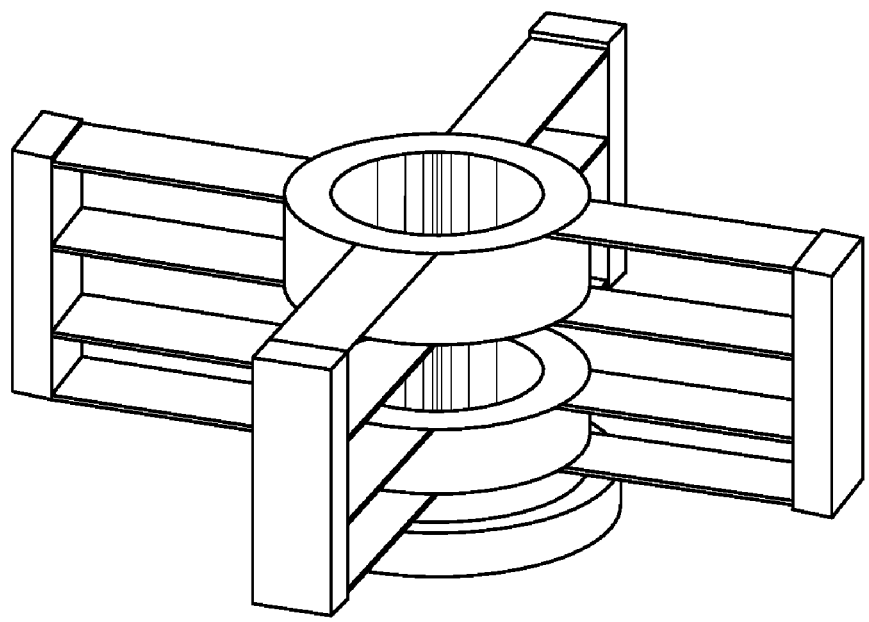
FIG. 2 is a perspective view of a compliant element in accordance with another embodiment of the invention.

Alternatively, the compliant element 14 may comprise other suitable structures with other shapes. FIG. 2 depicts a perspective view of the compliant element 14 in accordance with another embodiment of the invention. As depicted in FIG. 2, the compliant element 14 comprises a deformable single piece. Thus, with the deformation and restoration of the compliant element 14, the tip of the sensor 16 may move into or out of the compliant element 14.

As depicted in FIG. 1, the processor 15 is configured to process the signals from the coordinate measurement machine 11, the self-aligning probe assembly, and/or the sensor 16. It should be noted that the present invention is not limited to any particular processor for performing the processing tasks of the invention. The term "processor", as that term is used herein, is intended to denote any machine capable of performing the calculations, or computations, necessary to perform the tasks of the invention. The term "processor" is intended to denote any machine that is capable of accepting a structured input and of processing the input in accordance with prescribed rules to produce an output, as will be understood by those skilled in the art.

Additionally, the inspection system 10 may further comprise a monitor 18, such as a LCD connected to the processor 15 to display processed data from the processor 15. In certain embodiments, the inspection system 10 may not employ the monitor 18 and may instead provide a printout of the processed data or utilize any other technique for viewing the processed data. In other examples, the processor 15 may be incorporated in a device having the capability to display the processed data.

For the arrangement depicted in FIG. 1, the joint assembly 12 comprises a first joint assembly 20 and a second joint assembly 21. The first joint assembly 20 is coupled to the motion control device 11. The second joint assembly 21 is located between and coupled to the first joint assembly 20 and the probe housing 13. In certain example arrangements, the first joint assembly 20 may be excluded.

For some arrangements, the first joint assembly 20 may comprise a first joint 22. The first joint 22 may have one-degree of freedom (1-DOF) and be configured to facilitate the motion control device 11 to push the sensor 16 to contact an object to a certain degree. In the illustrated embodiment, the first joint 22 comprises a 1-DOF translational joint, such as a linear guide similar to the linear guide 14. Alternatively, the first joint 22 may comprise other suitable 1-DOF translational joint.

In the illustrated example, the first joint assembly 20 further comprises a trigger 23. The trigger 23 may be a mechanical trigger or an electrical trigger. In certain embodiments, the motion control device 11 may comprise a trigger circuit (not shown). Thus, when the sensor 16 contacts an object to a desired degree, the trigger 23 may send a signal to the processor 15, and then the processor 15 may send a trigger signal to trigger the trigger circuit in the motion control device 11 so that the motion control device 11 stops moving the sensor 16 to avoid damaging the sensor 16 and/or the motion control device 11.

For some arrangements, the second joint assembly 21 may comprise a second joint (not labeled) and one or more rotational transducers (not labeled). The second joint may comprise a rotational joint with two-degree of freedom (2-DOF), or other one or more suitable rotational joints including, but are not limited to a combination of two 1-DOF rotational joints. In the illustrated embodiment, the second joint assembly 21 comprises a joystick. The joystick comprises two 1-DOF rotational joints, two rotational transducers and a spring. Alternatively, other types of the 2-DOF rotational joysticks may be provided. The one or more rotational transducers may be configured to detect rotation angles of the second joint and send rotational signals to the processor 15 for facilitating determination of the position of the tip of the sensor 16, which can be readily implemented by one skilled in the art.

In some embodiments, it should be noted that the term "joint" in the first and second joints may indicate any suitable connecting element having one or more degrees of freedom and configured to couple to the motion control device 11 and/or the probe housing 13. Moreover, for some non-limiting arrangements, the first joint and the second joint may have the capabilities to return to respective neutral positions when unloaded.

Figure 3:
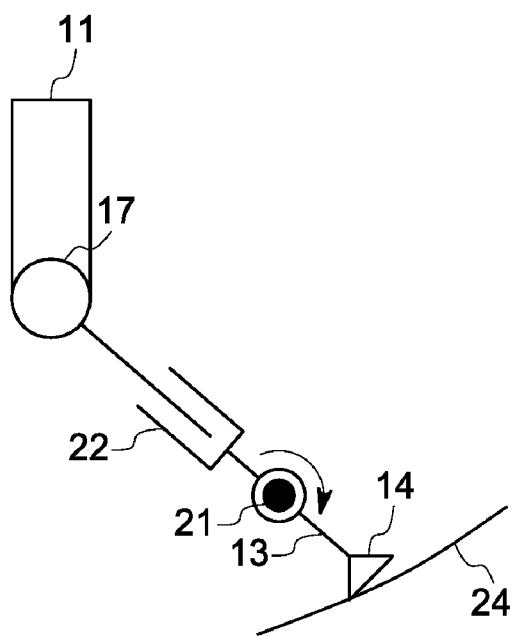
FIG. 3 is a schematic diagram illustrating an initial status of the inspection system contacting an object.
Figure 4:
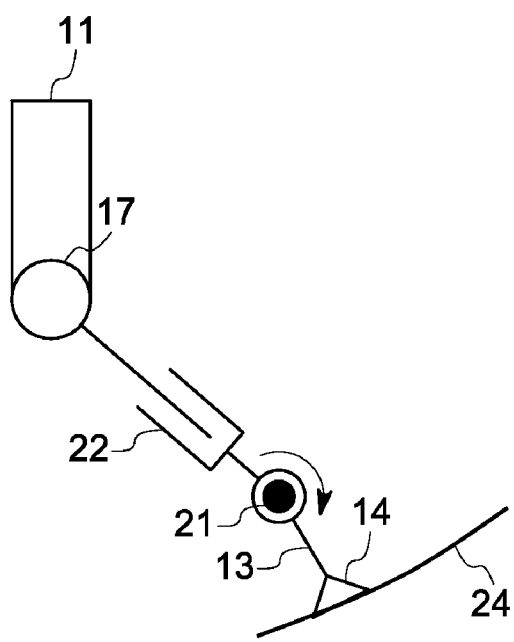
FIG. 4 is a schematic diagram illustrating a final status of the inspection system contacting the object.

FIGS. 3 and 4 are schematic diagrams illustrating an initial status and a final status of the inspection system 10 contacting an object 24. It should be noted that the schematic diagrams in FIGS. 3 and 4 are merely illustrative. For ease of illustration, the processor 15 and the monitor 18 are omitted in FIGS. 3 and 4.

As illustrated in FIG. 3, during operation, the motion control device 11 moves the self-aligning probe assembly equipped with the sensor 16 towards the object 24. When the sensor tip is not oriented normal to an inspected surface of the object 24, the compliant element 14 is compressed gradually and transfers off-centered pressure from the object 24 to the second joint assembly 21 to rotate the second joint until the compliant element 14 stably contacts the object 24, as illustrated in FIG. 4. In non-limiting examples, it should be noted that the term "off-centered pressure," as used herein, may indicate the pressure is off-centered from an axis of rotation of the second joint assembly 21.

Meanwhile, the motion control device 11 continues to push the self-aligning probe assembly, so that the springs in the first and/or second joints are also compressed until the tip of the sensor 16 moves beyond a bottom surface of the linear guide 14 to contact the object 24 to a desired degree. At this time, the trigger 23 sends a signal to the processor 15 to stop the movement of the motion control device 11 to protect the sensor 16 and/or the motion control device 11. The motion control device 11 and the one or more rotational transducers in the second joint assembly 21 may also send the movement signals and the rotation signals of the 2-DOF rotational joint, such as the joystick, to the processor 15. In some non-limiting applications, distances moved by the first joint 22 may be determined experimentally and may be set as a constant in the controller 15. Accordingly, the position and orientation of the sensor tip can be calculated in real time in the processor 15 based on the translational position (x, y, z) and rotational information from motion control device 11, together with the rotational and translation data from the joint assembly 12. Additionally, the sensor 16 may perform the desired inspection and feed the inspection data for the object 24 to processor 15 for processing. Thus, the processor 15 may take data inputs from the motion control device, the joint assembly and the sensor for processing in order to get the position and orientation of the sensor tip in real time, which may be used to move the sensor in contact with the object 24 and prevent collision therebetween. Furthermore, the contact or orientation between the sensor and the object may further ensure the accuracy of the non-destructive measurements and dimension measurements.

In some examples, since the compliant element 14 may have one degree of freedom, when the compliant element 14 stably contacts the object 24, the tip of the sensor 16 may be substantially normal or perpendicular to the surface of the object 24 to be inspected. Additionally, when the inspection system 10 is away from the object 24, the first joint 22, the second joint, and the compliant element 14 may restore themselves to their respective original status.

In some examples, in order to achieve relatively consistent contact between the tip of the sensor 16 and points on the object 24, the first joint assembly 20 may be disposed between the second joint assembly 21 and the probe housing 13. That is, the second joint assembly 21 may be connected to the motion control device 11, and the first joint assembly 20 may be connected to the second joint assembly 21 and the probe housing 13. Accordingly, in certain examples, since the first joint 22 and the compliant element 14 may have one degree of freedom and be connected to the probe housing 13, the sensor tip and the object 24 may have consistent contact.

In other examples, the first joint assembly 20 may comprise the first joint 22 and a translational transducer (not shown) instead of the trigger 23 to achieve the relatively consistent contact between the tip of the sensor 16 and the object 24. Thus, during operation, the translational and rotational transducers in the joint assembly 20 may send respective signals to the processor 15. The processor 15 may analyze the contact status of the sensor tip and the object 24 based on analysis of the signals from the transducers, so as to send a trigger signal to stop the movement of the motion control device 11. Additionally, the processor 15 may also calculate the position of the inspection point on the object 24 based on the signals from the transducers and the motion control device 11. For some arrangements, the first joint assembly 20 equipped with the translation transducer may be disposed between the motion control device 11 and the second joint assembly 21, or between the second joint assembly and the probe housing 13. In certain applications, the trigger 23 may also be provided in addition to the translational transducer.

In some embodiments, the springs or other elastic elements in the first joint and/or the second joint may function as buffers to prevent the sensor 16 from colliding with the object 24. Alternatively, the inspection system 10 may comprise one or more proximity sensors (not shown) in communication with the processor 15 to determine distances between the sensor 16 and the object 24 while the motion control device 11 moves the self-aligning probe assembly towards the object 24, so as to prevent the sensor 16 and the object 24 from colliding. Additionally, the one or more proximity sensors may be employed independently, or be integrated with the one or more sensors 16.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the subsequent claims.

What is claimed is:

1. An inspection system for performing non-destructive inspection of an object, the inspection system comprising:
 a sensor configured to acquire inspection data for the object;
 a motion control device;
 a joint assembly coupled to the motion control device;
 a probe housing coupled to the joint assembly and configured to hold the sensor;
 a compliant element coupled to the probe housing and configured to cooperate with the joint assembly and the motion control device to position the sensor relative to the object; and
 wherein the sensor is moveable relative to the compliant element.

2. The inspection system of claim 1, wherein the sensor is positioned to contact and to have an angle in a range of 90+/−5 degrees with an inspected surface of the object.

3. The inspection system of claim 1, wherein the sensor is selected from the group consisting of an ultrasound sensor, an eddy current sensor, an optical sensor, and combinations thereof.

4. The inspection system of claim 1, further comprising a processor configured to communicate with the sensor to process the inspection data for the object, and wherein the motion control device comprises a coordinate measurement machine.

5. The inspection system of claim 1, wherein the joint assembly comprise a first joint assembly and a second joint assembly coupled to the first joint assembly, and wherein one of the first and second joint assemblies is coupled to the motion control device and the other is coupled to the probe housing.

6. An inspection system for performing non-destructive inspection of an object, the inspection system comprising:
 a sensor configured to acquire inspection data for the object;
 a motion control device;
 a joint assembly coupled to the motion control device;
 a probe housing coupled to the joint assembly and configured to hold the sensor; and
 a compliant element coupled to the probe housing and configured to cooperate with the joint assembly and the motion control device to position the sensor relative to the object, wherein the joint assembly comprise a first joint assembly and a second joint assembly coupled to the first joint assembly, and wherein the first joint assembly is coupled to the motion control device and the second joint assembly is coupled to the probe housing.

7. An inspection system for performing non-destructive inspection of an object, the inspection system comprising:

a sensor configured to acquire inspection data for the object;
a motion control device;
a joint assembly coupled to the motion control device;
a probe housing coupled to the joint assembly and configured to hold the sensor; and
a compliant element coupled to the probe housing and configured to cooperate with the joint assembly and the motion control device to position the sensor relative to the object, wherein the joint assembly comprise a first joint assembly and a second joint assembly coupled to the first joint assembly, wherein the first joint assembly comprises a first joint and one of a trigger and a transducer, and wherein the trigger and the transducer are configured to control and inspect movement of the motion control device and the first joint, respectively.

8. The inspection system of claim 7, wherein the first joint comprises a translational joint having one-degree of freedom and the transducer comprises a translational transducer.

9. The inspection system of claim 8, wherein the first joint comprises a linear guide equipped with a spring.

10. An inspection system, for performing non-destructive inspection of an object, the inspection system comprising:
a sensor configured to acquire inspection data for the object;
a motion control device;
a joint assembly coupled to the motion control device;
a probe housing coupled to the joint assembly and configured to hold the sensor; and
a compliant element coupled to the probe housing and configured to cooperate with the joint assembly and the motion control device to position the sensor relative to the object, wherein the joint assembly comprise a first joint assembly and a second joint assembly coupled to the first joint assembly, and wherein one of the first and second joint assemblies is coupled to the motion control device and the other is coupled to the probe housing, wherein the second joint assembly comprises a second joint and one or more transducers, and wherein the one or more transducers are configured to inspect movement of the second joint.

11. The inspection system of claim 10, wherein the second joint comprises a rotational joint having two degrees of freedom or a combination of two rotational joints with one degree of freedom, and the one or more transducers comprise one or more rotational transducers.

12. The inspection system of claim 11, wherein the second joint comprises a joystick equipped with a spring.

13. An inspection system for performing non-destructive inspection of an object, the inspection system comprising:
a sensor configured to acquire inspection data for the object;
a motion control device;
a joint assembly coupled to the motion control device;
a probe housing coupled to the joint assembly and configured to hold the sensor; and
a compliant element coupled to the probe housing and configured to cooperate with the joint assembly and the motion control device to position the sensor relative to the object, wherein the compliant element is further configured to deform under pressure exerted by the object and to restore itself in the absence of the pressure.

14. The inspection system of claim 13, wherein the pressure is an off-centered pressure, and wherein the compliant element is further configured to transfer the off-centered pressure to and rotate the joint assembly to achieve stable contact with the object to facilitate positioning the sensor relative to the object.

15. The inspection system of claim 13, wherein the compliant element has one degree of freedom and comprises:
a linear guide equipped with a spring, or
a deformable single piece.

16. A self-aligning probe assembly comprising:
a joint assembly;
a probe housing coupled to the joint assembly and configured to hold a sensor;
a compliant element coupled to the probe housing and configured to cooperate with the joint assembly to facilitate aligning the sensor to contact an inspected surface of an object, and
wherein the compliant element is further configured to deform under pressure exerted by the object and to restore itself in the absence of the pressure.

17. A self-aligning probe assembly comprising:
a joint assembly;
a probe housing coupled to the joint assembly and configured to hold a sensor;
a compliant element coupled to the probe housing and configured to cooperate with the joint assembly to facilitate aligning the sensor to contact and to have angle in a range of 90+/−15 degrees with an inspected surface of an object, wherein the joint assembly comprises a first joint assembly and a second joint assembly coupled to the first joint assembly,
wherein the first joint assembly comprises a translational joint with one degree of freedom and one of a trigger and a rotational transducer, and
wherein the second joint assembly comprises one or more rotational transducers and either a rotational joint with two degrees of freedom or a combination of two rotational joints with one degree of freedom.

18. The self-aligning probe assembly of claim 17, wherein the first joint comprises a linear guide equipped with a spring, and the second joint comprises a joystick with a spring.

19. The self-aligning probe assembly of claim 17, wherein the compliant element is further configured to deform under pressure exerted by the object and to restore itself in the absence of the pressure, wherein the pressure is an off-centered pressure, and wherein the compliant element transfers the off-centered pressure to and rotates the second joint to achieve stable contact with the object to facilitate aligning the sensor to contact and be normal to the surface of the object.

20. The self-aligning probe assembly of claim 19, wherein the compliant element has one degree of freedom and comprises:
a linear guide equipped with a spring, or
a deformable single piece.

* * * * *